Figure 1:
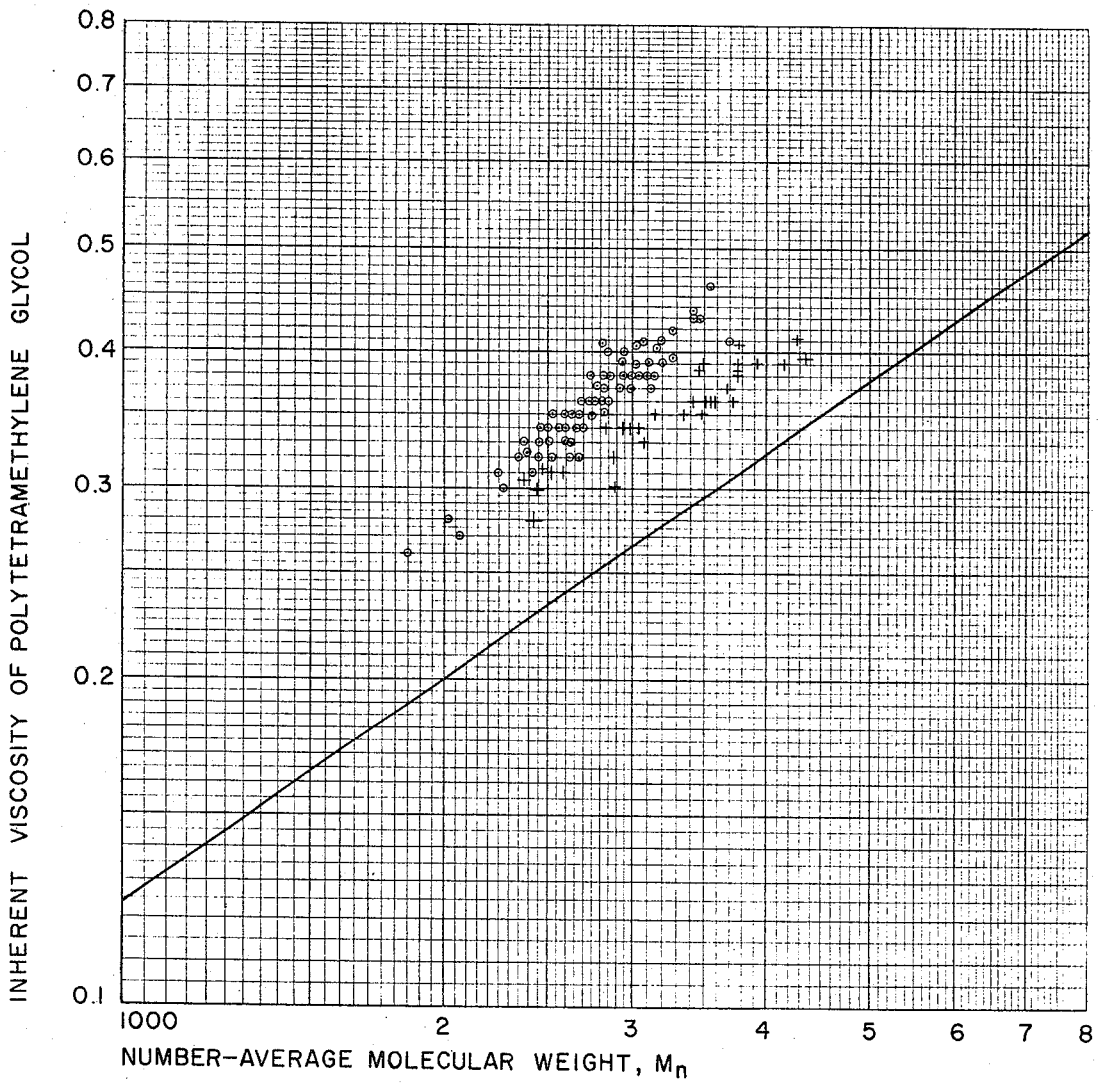
Figure 2:
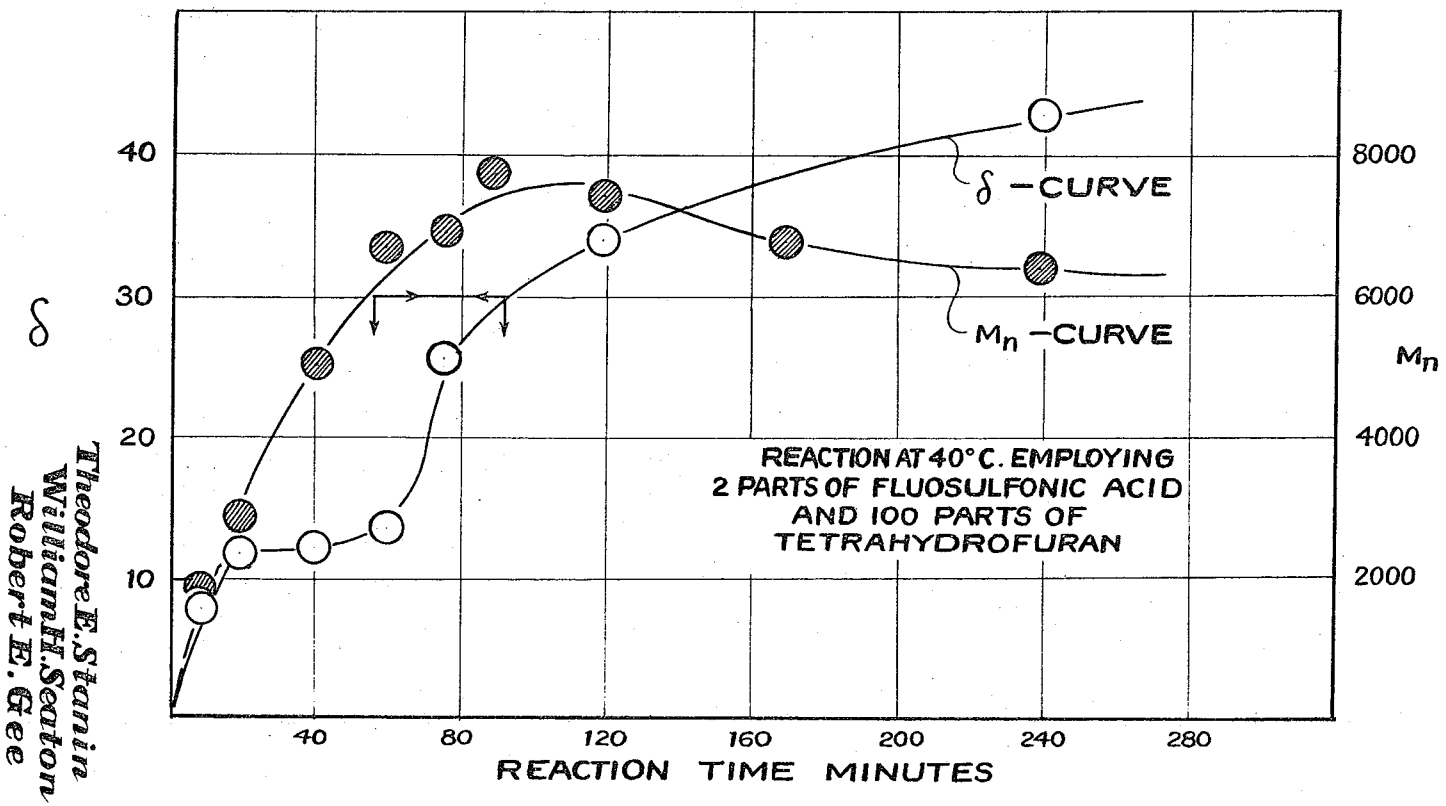

DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED SEPTEMBER 8, 1970

878 O.G. 239

T878,004

POLY(TETRAMETHYLENE GLYCOL) HAVING A NARROW MOLECULAR WEIGHT DISTRIBUTION AND ITS MANUFACTURE

William H. Seaton, Theodore E. Stanin, and Robert E. Gee, Jr., all of P.O. Box 511, Kingsport, Tenn. 37662

Continuation of application Ser. No. 822,832, Apr. 9, 1969, which is a continuation-in-part of application Ser. No. 627,558, Mar. 31, 1967, which, in turn, is a continuation of application Ser. No. 239,684, Nov. 23, 1962. This application Dec. 22, 1969, Ser. No. 883,666

Int. Cl. C07c *43/00*

U.S. Cl. 260—615

2 Sheets Drawing. 23 Pages Specification

Poly(tetramethylene glycol) compositions having a number-average molecular weight of 1,000 to 6,000 can be prepared by a process which comprises (1) continuously polymerizing tetrahydrofuran at a temperature from about 20° to about 65° C. within from 2 to 60 minutes in the presence of Lewis acids and (2) terminating the polymerization reaction before equilibrium is attained, that is, before the relative amounts of monomer and polymer in the reacting solution become constant at a definite temperature and pressure. The resulting polymeric compositions are characterized in having a narrow molecular weight distribution. The poly(tetramethylene glycol) compositions having a narrow molecular weight distribution which are produced according to the disclosed process are particularly valuable as glycol constituents in the production of elastomeric polyesters.

THEODORE E. STANIN
WILLIAM H. SEATON
ROBERT E. GEE
INVENTORS

BY

ATTORNEY

PERCENT DEVIATION AND NUMBER AVERAGE MOLECULAR WEIGHT VERSUS REACTION TIME

Theodore E. Stanin
William H. Seaton
Robert E. Gee
INVENTORS
BY R. Frank Smith
Charles L. Good
ATTORNEYS